United States Patent [19]

Neisse

[11] Patent Number: 5,078,598

[45] Date of Patent: Jan. 7, 1992

[54] DENTAL SHADE GUIDE

[75] Inventor: Daryl L. Neisse, Lake Elmo, Minn.

[73] Assignee: Minnesota Mining and Manufacturing Company, St. Paul, Minn.

[21] Appl. No.: 565,551

[22] Filed: Aug. 10, 1990

[51] Int. Cl.$^5$ .............................................. A61C 19/10
[52] U.S. Cl. ...................................................... 433/26
[58] Field of Search ........................ 433/26, 74, 202.1

[56] References Cited

U.S. PATENT DOCUMENTS

| | | | |
|---|---|---|---|
| 2,262,641 | 11/1941 | Hayward | 433/26 |
| 2,765,534 | 10/1956 | Bloom et al. | 433/26 |
| 2,805,478 | 9/1957 | Adams | 433/26 |
| 3,521,357 | 7/1970 | Berglund et al. | 433/26 |
| 4,618,325 | 10/1986 | Appelle | 433/26 |

OTHER PUBLICATIONS

Pyroplast, Williams-Justi Promotional Brochure, 1966.
"Suggestions for Shade Selection with Your New Trubyte Bioform Extended Range Shade Guide", Dents Ply Publication No. 8050001C (1973, 1983).
"Lumin Shade Guide", Vident.

Primary Examiner—Gene Mancene
Assistant Examiner—Michael Lynch
Attorney, Agent, or Firm—Gary L. Griswold; Walter N. Kirn; James D. Christoff

[57] ABSTRACT

A dental shade guide has a tooth-shaped first portion and an elongated second portion which is integrally connected to the first portion. The second portion varies in thickness in stepped fashion along its length. Both portions are made of a material having substantially the same color, thereby enabling the user to compare the color of the shade guide in differing degrees of opacity with the color of tooth structure adjacent the intended restoration, in order to increase the likelihood that the finished restoration will appear as aesthetic as possible.

11 Claims, 1 Drawing Sheet

DENTAL SHADE GUIDE

BACKGROUND OF THE INVENTION

1. Field of the Invention

This invention relates to a dental shade guide for matching the color of a dental material with a particular tooth.

2. Description of the Related Art

Dental restorations repair weakened, damaged or missing teeth. Direct placement restorations are made by applying a dental composite directly to damaged tooth structure. Indirect placement restorations, including inlays and onlays, are also often made of dental composites but are shaped outside of the oral cavity and then placed in or on the tooth structure. Restorations may also include crowns, bridges, implants, dentures and the like that comprise an artificial tooth or set of teeth which is secured in place in the oral cavity.

Preferably, dental restorations simulate as close as possible the appearance of remaining visible tooth structure in the patient's mouth so that the restoration looks as natural as possible. However, the color of teeth varies from individual to individual, and also varies somewhat from tooth to tooth in the mouth. As such, care must be undertaken to select a restorative material that has a color which is closely similar to the color of adjacent teeth.

Typically, a set of dental shade guides, each of a different color, is used to select a color for the restoration. The shade guides are held next to the teeth in order to facilitate comparison of the colors of the different guides with the color of tooth structure adjacent the restoration. Once a particular guide is chosen, indicia on the guide enable the dentist to choose restorative material with proper coloring or pigments so that the restoration, once completed and in the mouth, appears as aesthetic as practicable.

The nature and perception of color is somewhat subjective. Color may be measured by a visual technique, often called the Munsell Color System, which identifies three parameters: hue, value and chroma. Hue is measured on a numeric scale for each of the ten color families (such as red, yellow-red, yellow and the like). Value (or brightness) varies from black to white on a numeric scale and the value of a given color can be modified by the addition of a white pigment. Chroma (or saturation) is a measurement of the amount of color which is present at a given hue, and ranges on a numeric scale from 0 (which is achromatic or gray and has no color) to a fully saturated hue which is 18. The hue, chroma and value taken together define the color of an object under specified lighting conditions.

The perceived color of an object may be modified by the translucency or opacity of the object. Opacity is often measured in terms of a contrast ratio, which changes in a particular object in accordance with the thickness of the object. For more information, see, e.g., "Restorative Dental Materials", edited by Robert G. Craig and published in 1989 by C. V. Mosby Company of St. Louis, Miss.

To date, a variety of dental shade guides have been commercialized. One widely available guide is in the shape of an elongated, integrally molded bar which varies in thickness in stepped regions along the length of the bar. The bar is slightly translucent, and as a result the stepped regions vary in opacity even though the color of the material is the same throughout the bar. In this manner, an attempt can be made to match the color of the shade guide with the color of the teeth while also considering the opacity of differing regions of the shade guide and the teeth.

Other types of shade guides are molded in the shape of a tooth, and have a depending handle for holding the guide next to the patient's teeth. The handle is opaque or transparent and made of a material which is different in composition and color from the tooth-shaped portion. The tooth-shaped portion, being made of slightly translucent material, varies in opacity from thinner areas of the tooth to thicker tooth areas, although the color of the material remains the same throughout the tooth. Some dentists prefer to use the tooth-shaped shade guide, apparently because the lighting conditions and variations in opacity through the tooth-shaped guide resemble the same phenomena in natural teeth.

The selection of a proper color for dental restorations, however, is an art that is sometimes difficult for certain individuals to master. Moreover, the time and expense of making restorations discourages additional attempts to match colors if the color of the first restoration does not appear realistic in the mouth. Consequently, there is a continuing need for a dental shade guide which facilitates selection of the proper color.

SUMMARY OF THE INVENTION

The present invention concerns a dental shade guide having a first portion and a second portion connected to the first portion. The first portion has a generally tooth-shaped configuration. The second portion is elongated and has a thickness which varies along its length. The first portion and the second portion are each made of a material having substantially the same color.

In use, the shade guide is held next to the patient's teeth, and observation of the tooth-shaped portion and the elongated portion of the shade guide can be readily made and compared with the color of the patient's teeth. The elongated portion of the shade guide provides a relatively wide, flat expanse of surface area in varying degrees of opacity of the same color. The tooth-shaped portion, by contrast, reflects and transmits light in a manner similar to natural teeth. By visually comparing both the elongated portion and the tooth-shaped portion together, along with the patient's natural teeth, selection of the proper color is facilitated.

DETAILED DESCRIPTION OF THE PREFERRED EMBODIMENT

Figure 1:
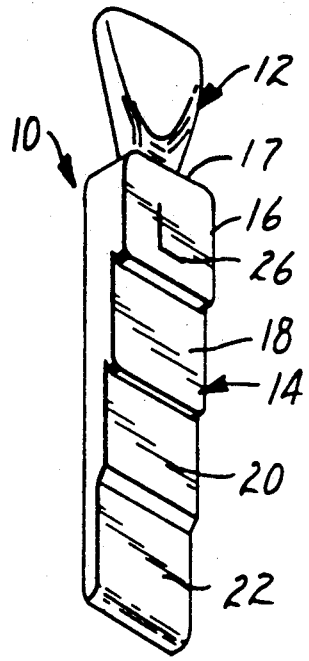
FIG. 1 is a perspective view of a dental shade guide constructed in accordance with the invention.
Figure 2:
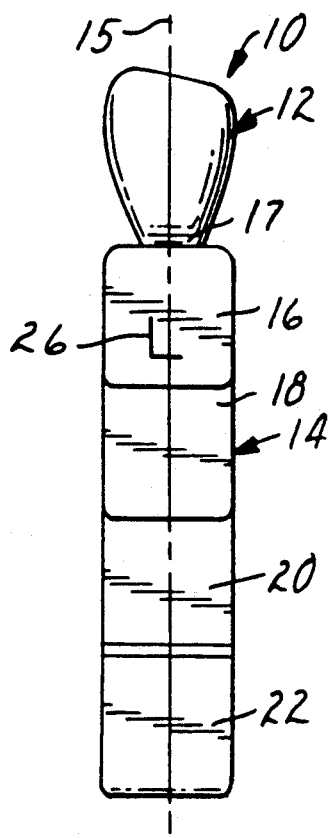
FIG. 2 is a front elevational view of the shade guide shown in FIG. 1.

A dental shade guide is broadly designated by the numeral 10 in FIGS. 1-4 and includes a first portion 12 and a second portion 14 connected to the first portion 12. The front of the first portion 12 has a tooth-shaped configuration, although a rear surface 11 (FIG. 4) of the first portion 12 is flat and planar with a rear surface 13 of the second portion 14 as shown, for example, in FIG. 3. The first portion 12 has a central axis 15 (FIG. 2)

which is aligned with the longitudinal axis of the second portion 14.

The second portion 14 is elongated and bar-shaped, and has a thickness which varies along its length. Specifically, the second portion 14 includes a first section 16 that is integral and directly connected with a base 17 of the tooth-shaped first portion 12, a second section 18 having a thickness less than the first section 16, a third section 20 having a thickness less than the second section 18, and a fourth, end-most section 22 which has a thickness less than the third section 20. Two grooves 24 formed on the back of the second portion 14 (see FIGS. 3 and 4) permit the shade guide 10 to be releasably snapped into a clip-type holder or stand (not shown) along with a number of shade guides of other colors.

The guide 10 is an integrally molded, unitary body that is made of a synthetic resinous material. A pigment is added to the synthetic resinous material so that the guide 10 has one of a number of colors which each match a corresponding color or shade of available restorative material. The synthetic resinous material is preferably polycarbonate which has long term color stability.

Figure 3:
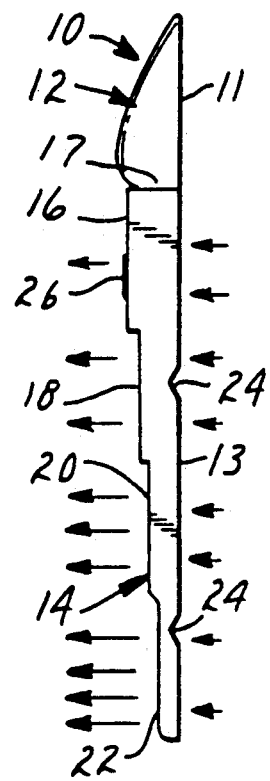
FIG. 3 is a side elevational view of the shade guide shown in FIGS. 1 and 2.
Figure 4:
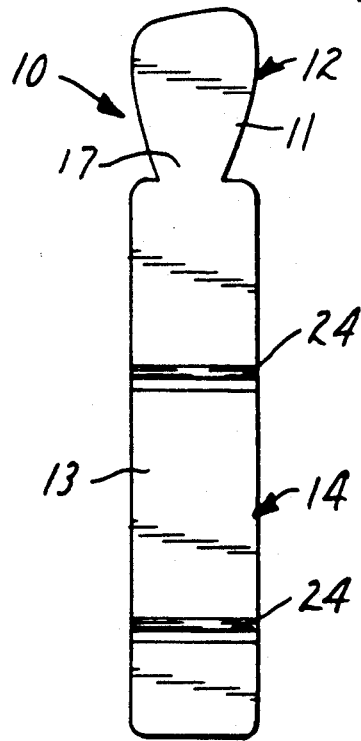
FIG. 4 is a rear elevational view of the shade guide shown in FIGS. 1-3.

The arrows in FIG. 3 schematically represent the relative degree of translucency of the four sections 16-22. The thickest, first section 16 is opaque or only very slightly translucent, and is thick enough to prevent substantially all of the light behind the flat rear wall of the first section 16 from passing through the guide 10. The fourth section 22, by contrast, is much thinner and therefore is more translucent than the first section 16, and permits correspondingly greater quantities of light to pass through the guide 10. The degree of translucency of the intermediate sections 18, 20 will fall between the translucency of the sections 16, 22 in approximate proportion to their relative, corresponding thicknesses.

Typically, the thickest, first section 16 is opaque or nearly opaque, such that its color is seen by light reflected from the flat, front surface of the first section 16. The thickness of the first section 16 is approximately equal to the thickness of the thickest section of the tooth-shaped first portion 12. In comparison, the color of the thinnest, fourth section 22 is seen partially by light reflected from its front surface, and partially by light transmitted through the fourth section 22, and the fourth section 22 has a translucency which approximates the translucency of the periphery of the tooth-shaped first portion 12 including a region along the upper edge of the same. Since the guide 10 is homogeneous in composition and integrally molded, the color (in terms of hue, value and chroma) of the material that comprises the guide 10 is substantially the same throughout the guide 10 although the opacity varies from a lower value in the fourth section 22 as well as thinner regions of the tooth-shaped first portion 12, to a relatively higher value in the first section 16 and thicker regions of the tooth-shaped first portion 12.

Advantageously, the first portion 12 is located directly next to the second portion 14 so that a quick visual check of the color of the shade guide 10 in different values of opacity can be made. Also, the tooth-shaped first portion 12, having a surface made of compound curves, reflects and transmits light in a fashion resembling natural teeth. As such, both the first portion 12 and the second portion 14 can be used together for visual comparison with the patient's natural teeth to ensure that the color of the selected shade guide 10 and hence of the restoration closely match the color of the tooth structure adjacent the restoration.

Normally, the dentist will have on hand a number of shade guides each similar to the shade guide 10 but of different colors. An indicia 26, molded in the fourth section 16, provides a code for selection of the restorative material which, when cured or hardened, will present a color identical or closely identical to the color of the guide 10.

I claim:

1. A dental shade guide having a first portion and a second portion connected to said first portion, said first portion having a generally tooth-shaped configuration, said second portion being elongated and having a thickenss which varies along its length for providing a varying translucency of said second portion with respect to a direction substantially coincident with said second portion elongation, said first portion and said second portion each made of a material having the same color.

2. The shade guide of claim 1, wherein said shade guide is elongated and wherein said first portion has a central axis aligned with the longitudinal axis of said second portion.

3. The shade guide of claim 2, wherein said tooth-shaped first portion has a base which is directly connected to said second portion.

4. The shade guide of claim 1, wherein said first portion and said second portion are integrally molded.

5. The shade guide of claim 1, wherein said first portion and said second portion are made of the same material.

6. The shade guide of claim 1, wherein said first portion and said second portion each have a flat rear surface.

7. The shade guide of claim 6, wherein said rear surface of said first portion is coplanar with said rear surface of said second portion.

8. The shade guide of claim 1, wherein said second portion has a first section of a certain thickness and a second section of a thickness less than said first section, and wherein said first portion is connected to said first section and is remote from said second section.

9. A dental shade guide having a first portion and a second portion connected to said first portion, said first portion having a generally tooth-shaped configuration, said second portion being elongated and having a thickness which varies along its length, said first portion and said second portion each made of a material having substantially the same color, said thickness of said second portion varying in stepped fashion along the length of said second portion.

10. A dental shade guide having a first portion and a second portion connected to said first portion, said first portion having a generally tooth-shaped configuration, said second portion being elongated and having a thickness which varies along its length for providing a varying translucency of said second portion with respect to a direction substantially coincident with said second portion elongation, said first portion and said second portion being integral and made of the same material.

11. A dental shade guide having a first portion and a second portion connected to said first portion, said first portion having a generally tooth-shaped configuration, said second portion being elongated and having a thickness which varies along its length, said first portion and said second portion being integral and made of substantially the same material, said thickness of said second portion varying in stepped fashion along the length of said second portion.

* * * * *